United States Patent
Matsui et al.

(10) Patent No.: US 11,325,112 B2
(45) Date of Patent: May 10, 2022

(54) METHOD OF FORMING INORGANIC NANOCAGES

(71) Applicant: Research Foundation of the City University of New York, New York, NY (US)

(72) Inventors: Hiroshi Matsui, Glen Rock, NJ (US); Zengyan Wei, Corona, NY (US); Justin Fang, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 67 days.

(21) Appl. No.: 16/876,206

(22) Filed: May 18, 2020

(65) Prior Publication Data
US 2020/0346198 A1 Nov. 5, 2020

Related U.S. Application Data

(63) Continuation-in-part of application No. 15/477,601, filed on Apr. 3, 2017, now Pat. No. 10,688,556.

(60) Provisional application No. 62/316,848, filed on Apr. 1, 2016.

(51) Int. Cl.
| | |
|---|---|
| *B01J 23/44* | (2006.01) |
| *B01J 23/52* | (2006.01) |
| *B01J 31/28* | (2006.01) |
| *B01J 35/00* | (2006.01) |
| *B01J 31/06* | (2006.01) |
| *A61K 49/18* | (2006.01) |

(52) U.S. Cl.
CPC .............. *B01J 31/28* (2013.01); *B01J 23/44* (2013.01); *B01J 23/52* (2013.01); *B01J 31/06* (2013.01); *B01J 35/0013* (2013.01); *A61K 49/1824* (2013.01); *B01J 2231/4211* (2013.01); *B01J 2531/005* (2013.01)

(58) Field of Classification Search
None
See application file for complete search history.

(56) References Cited

U.S. PATENT DOCUMENTS

| | | | |
|---|---|---|---|
| 5,262,176 A | 11/1993 | Palmacci et al. | |
| 6,974,707 B1 * | 12/2005 | Barie | C12Q 1/002 436/529 |
| 8,227,628 B2 | 7/2012 | Messersmith et al. | |
| 2010/0087622 A1 | 4/2010 | Messersmith et al. | |

(Continued)

OTHER PUBLICATIONS

Nanoscience NY, Abstracts of invited speakers at the Soft Nano event of the Nanoscience Initiative at CUNY's Advanced Science Research Center, Jun. 18, 2015.*

(Continued)

*Primary Examiner* — George Wyszomierski
(74) *Attorney, Agent, or Firm* — Peter J. Mikesell; Schmeiser, Olsen & Watts, LLP

(57) ABSTRACT

Nanocages are formed by etching nanocubes. The nanocubes are added to an aqueous system having an amphiphilic lipid dissolved in an organic solvent (e.g. a hydrophobic alcohol) to form reverse micelles. As the water evaporates the micelles shrink as etching of the flat surface of the nanocubes occurs. In this fashion hollow nanocages are produced. In one embodiment, the nanocage is covalently attached to a polymer shell (e.g. a dextran shell).

4 Claims, 12 Drawing Sheets

(56) References Cited

U.S. PATENT DOCUMENTS

| | | |
|---|---|---|
| 2010/0228237 A1 | 9/2010 | Chung et al. |
| 2010/0255311 A1 | 10/2010 | Lee et al. |
| 2013/0023714 A1* | 1/2013 | Johnston .............. A61P 35/00 600/1 |
| 2017/0152549 A1* | 6/2017 | Shih ................ G01N 33/54373 |
| 2018/0214943 A1 | 8/2018 | Xia et al. |
| 2018/0316023 A1 | 11/2018 | Fang et al. |

OTHER PUBLICATIONS

Skrabalak, S.E. et al., "Gold Nanocages for Biological Applications", Advanced Materials, vol. 19, issue 20, Oct. 2007, pp. 3177-3184.*

Wei, Z. et al.; Rational strategy for shaped nanomaterial synthesis in reverse micelle reactors; Nature Communications; May 14, 2014; pp. 1-8; 5:3870 | DOI: 10.1038/ncomms4870.

Rampersaud, S et al.; The Effect of Cage Shape on Nanoparticle-Based Drug Carriers: Anticancer Drug Release and Efficacy via Receptor Blockade Using Dextran-Coated Iron Oxide Nanocages; Nanoletters; Nov. 2, 2016; pp. A-G; DOI: 10.1021/acs.nanolett.6b02577.

Oh, M et al.; Galvanic Replacement Reactions in Metal Oxide Nanocrystals; Science; May 24, 2013; pp. 964-968; vol. 340.

Uchida, M. et al.; A Human Ferritin Iron Oxide Nano-composite Magnetic Resonance Contrast Agent; Magnetic Resonance in Medicine; 2008; pp. 1073-1081; vol. 60.

Liu, Z. et al.; Acetonide protection of dopamine for the synthesis of highly pure N-docosahexaenoyldopamine; Tetrahedron Letters; Feb. 20, 2010; pp. 2403-2405; vol. 51; Elsevier Ltd.

Jin, M. et al.; Palladium Concave Nanocubes with High-Index Facets and Their Enhanced Catalytic Properties; Angew. Chem. Int. Ed.; 2011; pp. 7850-7854; vol. 50; Wiley-VCH Verlag GmbH & Co. KGaA, Weinheim.

Niu, W. et al.; Seed-Mediated Growth of Nearly Monodisperse Palladium Nanocubes with Controllable Sizes; Crystal Growth & Design; Sep. 25, 2008; pp. 4440-4444; vol. 8, No. 12; American Chemical Society.

Chen, J. et al.; Gold Nanocages: Engineering Their Structure for Biomedical Applications; Advanced Materials; 2005; pp. 2255-2261; vol. 17; Wiley-VCH Verlag GmbH & Co. KGaA, Weinheim.

Yavuz, M. et al.; Gold nanocages covered by smart polymers for controlled release with near-infrared light; Nature Materials; Nov. 1, 2009; pp. 935-939; vol. 8.

Wang, F. et al.; Heteroepitaxial Growth of High-Index-Faceted Palladium Nanoshells and Their Catalytic Performance; J. Am. Chem. Soc.; Dec. 21, 2010; pp. 1106-1111; vol. 133.

Chen, H. et al.; Shape- and Size-Dependent Refractive Index Sensitivity of Gold Nanoparticles; Langmuir; Apr. 25, 2008; pp. 5233-5237; vol. 24; American Chemical Society.

Amstad, E. et al.; Stabilization and functionalization of iron oxide nanoparticles for biomedical applications; Nanoscale; 2001; pp. 2819-2843; vol. 3; The Royal Society of Chemistry.

Amstad, E. et al.; Ultrastable Iron Oxide Nanoparticle Colloidal Suspensions Using Dispersants with Catechol-Derived Anchor Groups; Nanoletters; Oct. 16, 2009; pp. 4042-4048; vol. 9, No. 12; American Chemical Society.

Niu, W. et al.; Shape-Controlled Synthesis of Single-Crystalline Palladium Nanocrystals; ACSNano; Mar. 2, 2010; pp. 1987-1996; vol. 4 • No. 4; American Chemical Society.

Choi, R. et al.; Thiolated Dextran-Coated Gold Nanorods for Photothermal Ablation of Inflammatory Macrophages; Lanmuir; Oct. 7, 2010; pp. 17520-17527; vol. 26 Issue 22; DOI: 10.1021/la1029728.

Park, J. et al.; Mussel-inspired modification of dextran for protein-resistant coating of titanium oxide; Carbohydrate Polymers; Jun. 2, 2013; pp. 753-757; vol. 97.

Varallyay, P et al.; Comparison of Two Superparamagnetic Viral-Sized Iron Oxide Particles Ferumoxides and Ferumoxtran-10 with a Gadolinium Chelate in Imaging Intracranial Tumors; AJNR Am J Neuroradiol; Apr. 2002; pp. 510-519; vol. 23.

An, K. et al.; Synthesis of Uniform Hollow Oxide Nanoparticles through Nanoscale Acid Etching; Nano Letters; Nov. 14, 2008; pp. 4252-4258; vol. 8 No. 12.

Cho, W. et al.: Acute toxicity and pharmacokinetics of nm-sized PEG-coated gold nanoparticles; Toxicology and Applied Pharmacology; Jan. 2009; pp. 16-24; vol. 236.

* cited by examiner

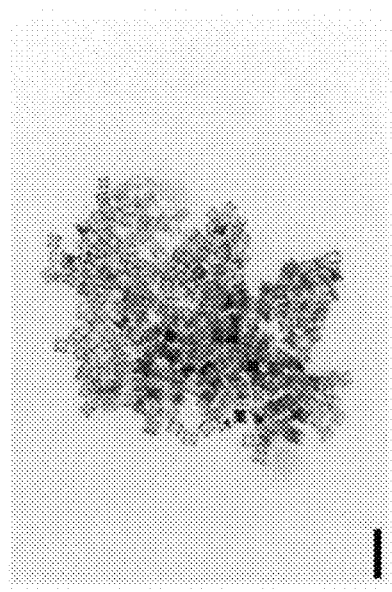
FIG. 4A
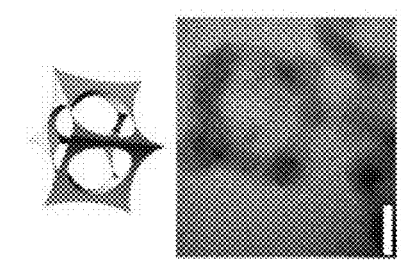
FIG. 4B
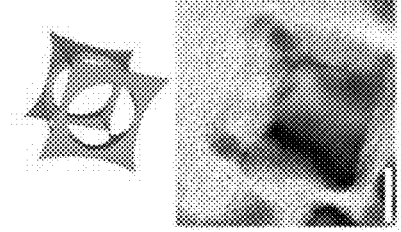
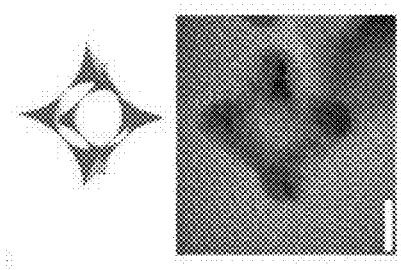
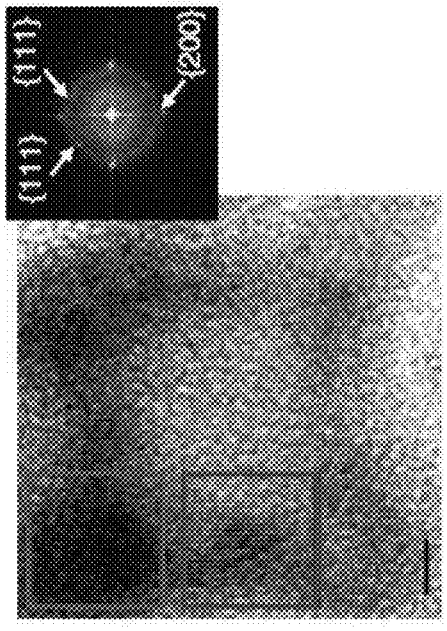
FIG. 4C
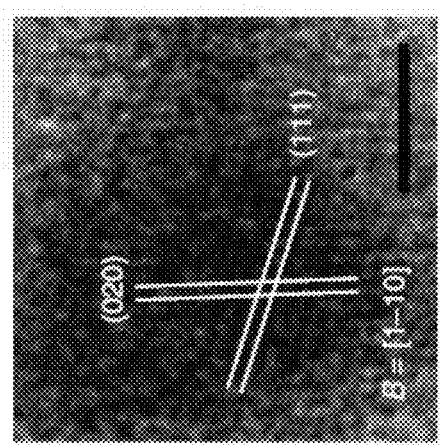
FIG. 4D
FIG. 4E

METHOD OF FORMING INORGANIC NANOCAGES

CROSS-REFERENCE TO RELATED APPLICATIONS

This application claims priority to and is a continuation-in-part of U.S. patent application Ser. No. 15/477,601 (filed Apr. 3, 2017) which is a non-provisional of U.S. Patent Application 62/316,848 (filed Apr. 1, 2016), the entirety of which are incorporated herein by reference.

STATEMENT OF FEDERALLY SPONSORED RESEARCH OR DEVELOPMENT

This invention was made with government support under contract number DE-FG-02-01ER45935 awarded by the U.S. Department of Energy. Support was also provided under contract number MD007599 awarded by the National Institute on Minority Health and Health Disparities (National Institute of Health). The government has certain rights in the invention.

BACKGROUND OF THE INVENTION

Metal nanoparticles have been synthesized in various shapes due to their applications in medical imaging, medical therapeutics, catalysis and plasmonics. However, rational synthesis of nanoparticles with sizes of 10 nm or less with specific shapes is a technical challenge. In medical fields, the progress of drug delivery with nanoparticle carriers is halted by the difficulty of crossing biobarriers (such as the blood brain barrier (BBB)) and achieving long circulation for both active and passive targeting. Nanoparticle platforms as small as 10 nm that conjugate specific molecules, for purposes of biobarrier crossing and improved biodistribution, would be a significant improvement for the therapeutic uses of cancer and neurological treatments.

The discussion above is merely provided for general background information and is not intended to be used as an aid in determining the scope of the claimed subject matter.

BRIEF DESCRIPTION OF THE INVENTION

Nanocages are formed by etching nanocubes. The nanocubes are added to an aqueous system having an amphiphilic lipid dissolved in an organic solvent (e.g. a hydrophobic alcohol) to form reverse micelles. As the water evaporates the micelles shrink as etching of the flat surface of the nanocubes occurs. In this fashion hollow nanocages are produced. In one embodiment, the nanocage is covalently attached to a polymer shell (e.g. a dextran shell).

In a first embodiment, a method of forming a nanocage is provided. The method comprising steps of: forming a reverse micelle system comprising an inorganic nanocube having a diameter of 15 nm or less, an amphiphilic lipid, water and an organic solvent that is immiscible with water and has a boiling point greater than 100° C.; removing the water by evaporation, the step of removing causing the inorganic nanocube to be etched to form a nanocage, wherein the nanocage has a diameter less than the diameter of the inorganic nanocube; and covalently attaching a polymer shell to the nanocage, wherein the polymer shell has a diameter of less than 50 nm.

In a second embodiment, a method of forming a nanocage is provided. The method comprising sequential steps of: forming a reverse micelle system comprising an inorganic nanocube consisting of iron oxide having a diameter of 15 nm or less, an amphiphilic lipid, water and an organic solvent that is immiscible with water and has a boiling point greater than 100° C.; removing the water by evaporation, the step of removing causing the inorganic nanocube to be etched to form an iron oxide nanocage, wherein the iron oxide nanocage has a diameter less than the diameter of the inorganic nanocube; and covalently attaching a polymer shell to the iron oxide nanocage, wherein the polymer shell comprises dextran and has a diameter of less than 50 nm and the iron oxide nanocage is covalently attached to the polymer shell by a catechol linking group.

In a third embodiment, a composition of matter is provided. The composition comprising: an inorganic nanocage with a diameter less than 15 nm; and a polymer shell comprising dextran surrounding the inorganic nanocage, wherein the polymer shell has a diameter of less than 50 nm and the inorganic nanocage is covalently attached to the polymer shell by a catechol linking group.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 4A is a TEM image of hollow nanocages;

FIG. 4B shows TEM images of individual nanocages at different angles;

FIG. 4C is a HRTEM image of FIG. 4B;

FIG. 4D shows a vacancy separating two crystalline zones at the edge region highlighted with a square in FIG. 4C;

FIG. 4E shows that lattice fringes corresponding to (020) and (111) planes of fcc Pd at the edge region highlighted with a red square in FIG. 4C;

DETAILED DESCRIPTION OF THE INVENTION

Figure 1:
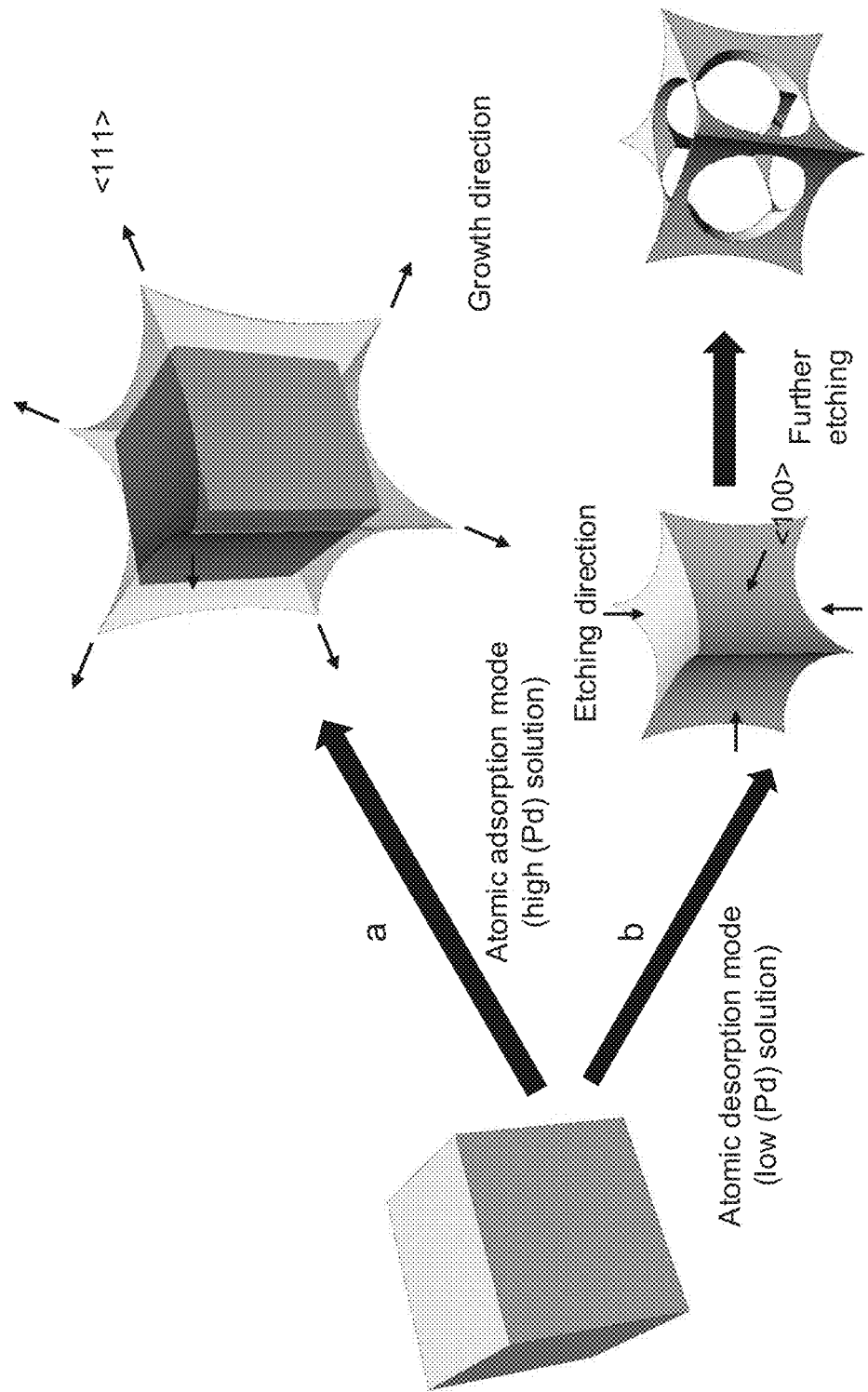
FIG. 1 depicts two alternative pathways showing atomic adsorption and atomic desorption modes.

This disclosure provides a methodology to fabricate small nanoparticles by evolving shapes thermo-dynamically. This method enables a more rational approach to fabricate shaped nanoparticles by etching specific positions of atoms on facets of seed nanocrystals in reverse micelle reactors where the surface energy gradient induces desorption of atoms on specific locations on the seed surfaces. For example, from seeds of 12 nm palladium nanocubes, the shape was evolved to concave nanocubes and finally hollow nanocages in the size of about 10 nm by etching the center of facets. In one embodiment, the resulting nanocages have a diameter of less than 15 nm. The high surface area-to-volume ratio and the exposure of a large number of palladium atoms on ledge and kink sites of hollow nanocages are advantageous to enhance catalytic activity and recyclability.

Previously, the evolution of the size of spherical inorganic nanoparticles (NPs) via atomic adsorption/desorption processes has been rationally established in one-phase solutions. The size-dependent solubility of NPs in the solution is illustrated by the Gibbs-Thomson equation:

$$S_r = S_\infty \exp\left(\frac{2\alpha V_m}{rRT}\right) \quad (1)$$

where $S_r$ and $S_\infty$ are solubility of the NP and its bulk counterpart, $\alpha$ is the specific surface energy, $V_m$ is the molar volume of NPs, r is the particle radius, R is the gas constant and T is the absolute temperature. In the condition of particle growth under a given precursor concentration ($S_b$), an equilibrium particle radius (r*) is derived from Equation 1:

$$r^* = \frac{2\alpha V_m}{RT\ln\left(\frac{S_b}{S_\infty}\right)} \quad (2)$$

To correlate the size change of NPs and ion concentration in solution for predicting the shape evolution of NPs in a typical diffusion control growth reaction, d(Δr)/dt is derived as:

$$\frac{d(\Delta r)}{dt} \cong \frac{K_D \Delta r}{\tilde{r}^2}\left(\frac{2}{\tilde{r}} - \frac{1}{r^*}\right) \quad (3)$$

where Δr is the s.d. of size distribution, $K_D$ is a constant and $\tilde{r}$ is the mean radius of NPs. From these equations, three important factors to control atomic adsorption on seed nanocrystals can be derived: (1) ion precursor concentration in solution, (2) distribution of high/low surface energy of crystalline facets on seeds and (3) topological shape of seeds. To promote the particle growth in the narrow size distribution with atomic adsorption, it is important to maintain the condition where the precursor concentration is relatively high because $\tilde{r}/2$ in Equation 3 needs to be larger than r* and r* monotonically decreases with increasing $S_b$ in Equation 2.

On the contrary, etching and desorption mode of atoms from the seed NPs becomes thermodynamically favorable when the precursor concentration is low (that is, $\tilde{r} \ll r^*$), which is the scope of the disclosed method. In addition, the surface energy is also important to determine adsorption/desorption of atoms from specific crystalline facets of seeds; when surface atoms on seed nanocrystals are exposed to solution under the minimal influence of capping agents (that is, low coverage and disorder of capping structures), desorption of atoms on high-energy crystalline facets is promoted while re-adsorption could become more dominant on low-energy crystalline facets, dependent upon the reactivity of desorbed species. Owing to this feature, the surface energy landscape created by the distribution of facets displaying distinct surface energy can direct the shape evolution of seeds. Furthermore, the topological shape of seed nanocrystals can also affect the thermodynamic adsorption/desorption of atoms on surfaces. For example, Equation 1 shows that the solubility of atoms from the crystalline facet is dependent on the geometric curvature of the NPs (r in Equation 1). Atoms on concave surfaces have distinct desorption property as compared with flat and convex surfaces. Thus, the application of shaped nanocrystals as seeds gives one a new toolbox for designing NPs in complex structures by controlling atomic adsorption/desorption in more precise patterns. In addition, fabricating NPs in complex shapes by optimizing three factors for the shape evolution from seed nanocrystals leads to rationale pathways for designing novel NPs. While polyhedron-shaped NPs are dominant for the use as seeds via reduction of ionic precursors, spherical seeds delocalize the surface energy landscape and thus the shape evolution tends to be simply dependent on the distribution of crystalline faces. Since the number of displayed crystalline faces is limited on the spherical nanocrystals, it is desirable to use the faceted seed nanocrystals for more delocalized surface energy distribution if the shape needs to be rationally evolved into more complex structures through atomic adsorption/desorption. Fortunately, seeds are now available in a variety of non-spherical shapes with high monodispersity because of the recent progress in shape-controlled NP synthesis. As explained above, the advantage for the use of non-spherical seed nanocrystals is to add predictable surface energy gradient based on their shape. Previously, various shaped NPs were grown by adsorbing atoms on low-energy facet of the seed nanocrystals in high precursor concentration. A one-pot solvothermal method was also applied to synthesize, for example, concaved platinum (Pt) nanoframes by mediating the concentration of capping agent. Through the atomic adsorption approach, concaved palladium (Pd) nanocubes were also grown by adsorbing Pd atoms kinetically on {111} facets while high-energy {200} facets were capped (See FIG. 1, path A). These approaches are suitable to grow large sized NPs; however, it is difficult to produce concave and hollow NPs in the size smaller than 15 nm since the size and quality of seeds limit the final dimension via the atomic adsorption mode. To fabricate smaller shaped NPs, chemical etchants were used to etch atoms on high-energy facets; however, the use of etchants makes the etching reaction chemistry complicated, sensitively dependent on the type of etchants and their concentration, and the interfacial dynamics of capping agents on selected crystalline facets also adds another complexity. Previously, the shape of gold (Au) NPs was transformed from nanorods to nanospheres by desorbing capping agents by heating because atoms on the high-energy surface migrate to lower surface energy facet. The aspect ratio of cadmium selenide (CdSe) nanorods was also changed by transferring surface atoms to lower surface energy facets through the interparticle ripening route. The disclosed method provides complex-shaped NPs using the rational synthesis pathway by balancing the surface energy landscape and the topological shape of seed nanocrystals: if the seed nanocrystals display well-defined surface energy distribution among crystalline facets, the resulting shape of nanocrystals after atomic desorption is predictable.

In the disclosed method, the shape of small seed nanocubes is evolved to concave nanocubes and finally hollow nanocages in the size of less than 15 nm by etching specific positions of atoms on facets of seed nanocrystals based on the surface energy distribution in reverse micelle reactors (FIG. 1, path B). The high surface area-to-volume ratio and the exposure of a large number of atoms on ledge and kink sites of hollow nanocages enhance catalytic activity and recyclability in Suzuki coupling reactions.

Nanocubes (i.e. cubes with a diameter of 100 nm or less) can be formed from inorganic nanoparticles (i.e. particles with a diameter of 100 nm or less) using conventional methodology. The nanocubes are metals or metal oxides such as Pd, Au or iron oxides (e.g. $Fe_2O_3$). Nanocubes can be formed, for example, by mixing metallic ions (e.g. $Na_2PdCl_4$) with an amphiphilic lipid in an aqueous solution. The amphiphilic lipid prevents aggregation. This lipid-capped nanotubes are incorporated in a lipid-water micelle. The ratio of lipid to water may be adjusted to ensure a clear reverse micelle solution is formed but the ratio is otherwise not critical.

Once the nanocubes are formed in the aqueous solution then the etching can be performed by first adding an amphiphilic lipid dissolved in an organic solvent (e.g. a hydrophobic alcohol) and then evaporating the water. The organic solvent should be immiscible with water such that micelles may be formed. The volume and ratios of the amphiphilic lipid and the organic solvent are not critical provided a clear reverse micelle is formed. Additionally, the organic solvent should have a boiling point greater than that of water (i.e. greater than 100° C.). In one embodiment, the organic solvent has a boiling point greater than 150° C. The amphiphilic lipid may be the same or different than the amphiphilic lipid used in the formation of the nanocubes. The amphiphilic lipid should be both stable at 105° C. and stabilize a water in oil reverse micelle solution. Examples of suitable amphiphilic lipids include cetyl-trimethylammonium bromide, hexadecyl trimethyl ammonium chloride, sodium dodecyl sulfate, sodium dodecyl benzene sulfonate, oleic acid and oleylamine.

After the amphiphilic lipid and the organic solvent are added the water is evaporated. Heating may facilitate evaporation of the water. Because the organic solvent was selected to have a boiling point greater than that of water, the water will evaporate before the organic solvent evaporates. In one embodiment, the system is heated to a temperature greater than 80° C. to remove the water. In another embodiment, the system is heated to a temperature greater than 90° C. In another embodiment, the system is heated to the boiling point of water.

Figure 2A:
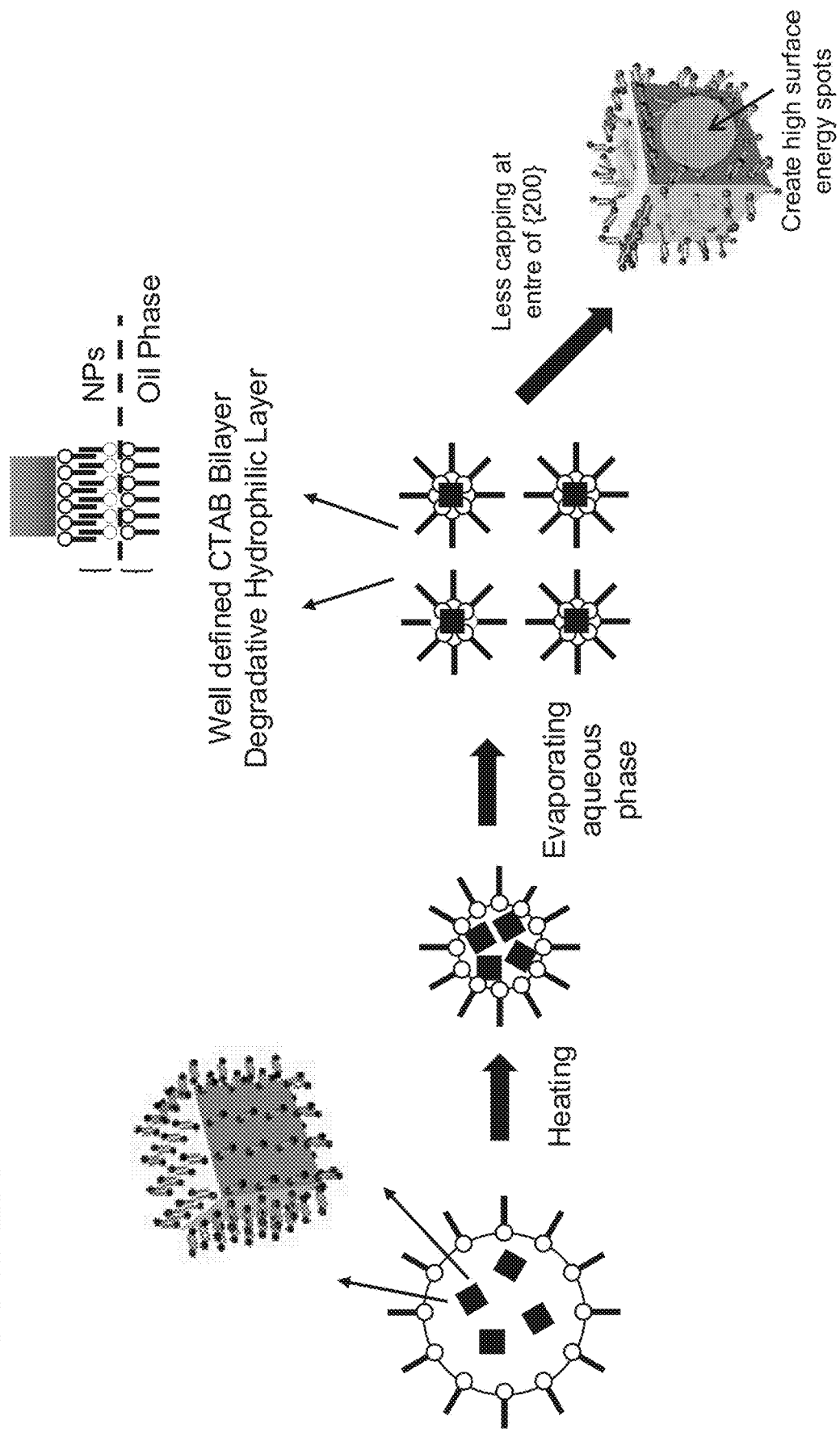
FIG. 2A is method showing generation of a reverse micelle using a nanocube.
Figure 2B:
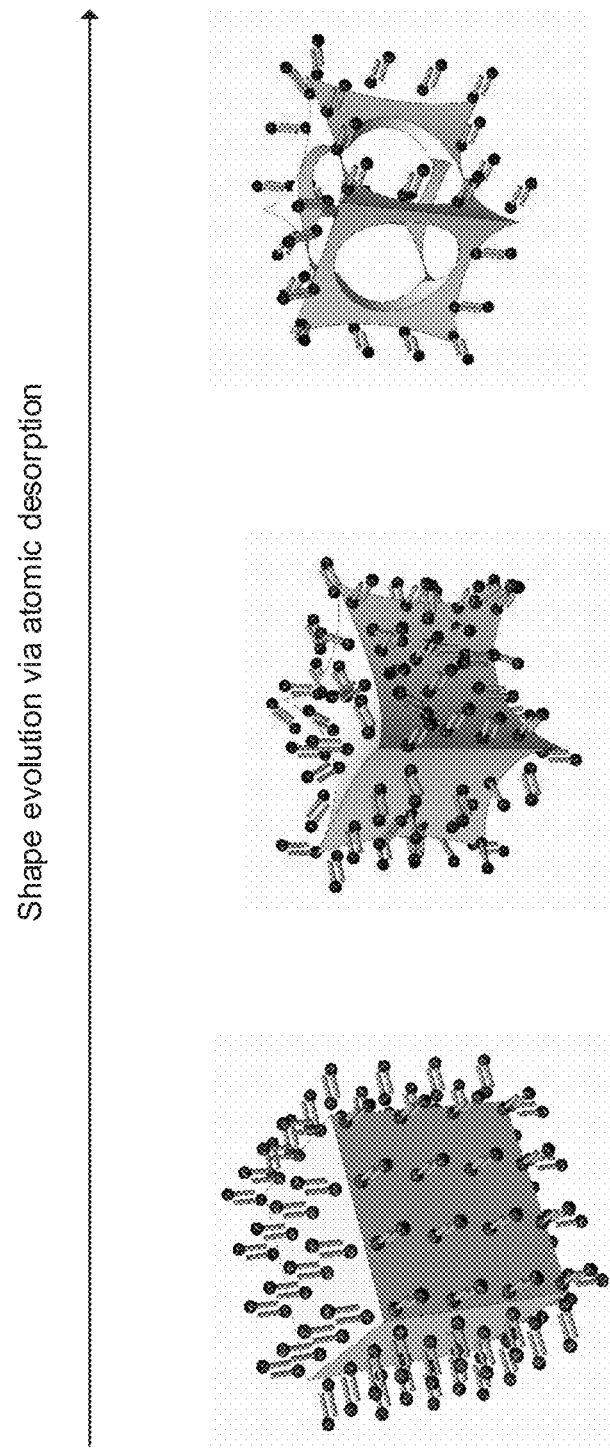
FIG. 2B depicts the synthesis of a nanocage from a nanocube.

An example of the etching strategy is summarized in FIG. 2A. The seeds of Pd nanocubes are dispersed in aqueous compartment of reverse micelle. The Pd nanocube seeds are hydrophilic as their {200} facets are protected by a well-defined bilayer of an amphiphilic lipid such as cetyl-trimethylammonium bromide (CTAB; FIG. 2A). Next, heating slowly evaporates the water phase. The hydrophilic compartment becomes smaller and eventually transformed into one single layer of CTAB whose polar headgroups directly contact the well-defined bilayer of CTAB on the NPs. Diffusion of the organic solvent destabilizes this structure. Reduction in coverage and disorder in the packing structure of this structure occur more dominantly at the center of {200} facets. As a result, desorption of Pd atoms from the surface of seeds is triggered because of the surface energy gradient. In addition, the formation of stable Pd complexes between desorbed Pd atoms and CTAB in solution further promotes the release of Pd atoms and discourages the re-adsorption of Pd atoms on the seeds. This strategy enables the localized etching of Pd atoms on the nanocube seeds, and it creates concaved nanocubes and then the shape is further evolved into nanocages as shown in FIG. 2B.

The Pd nanocubes were prepared in an aqueous solution at 95° C. After sodium tetrachloropalladate(II) ($Na_2PdCl_4$), sodium hydroxide (NaOH) and CTAB were dissolved in water and stirred vigorously at 95° C. a freshly prepared ascorbic acid solution was immediately injected into the reaction system. The reaction was kept at 95° C. for 30 min. The product was collected using centrifugation and was washed with water. Transmission electron microscopy (TEM) image shows that as-prepared Pd nanocubes have an average size and the size distribution of 12 nm and less than 10%, respectively. High-resolution TEM (HRTEM) image reveals the single crystal characteristics of the nanocubes with the lattice fringe spacing at 2.0 Å, corresponding to the {200} planes of face centered cubic (fcc) Pd. The indexed fast Fourier transform (FFT) pattern (not shown) is consistent with the single crystalline pattern of the Pd nanocubes.

Figure 3B:
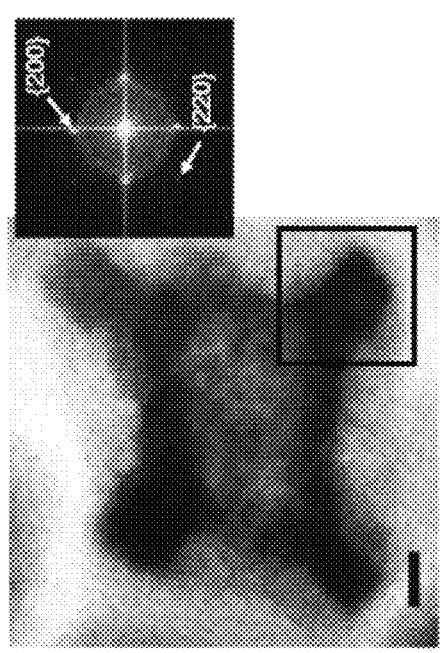
FIG. 3B is a HRTEM image of a Pd nanocage showing darker contrasts at the corners, indicating that the sample is thicker at the corners and is thinner in between after the etching treatment.
Figure 3A:
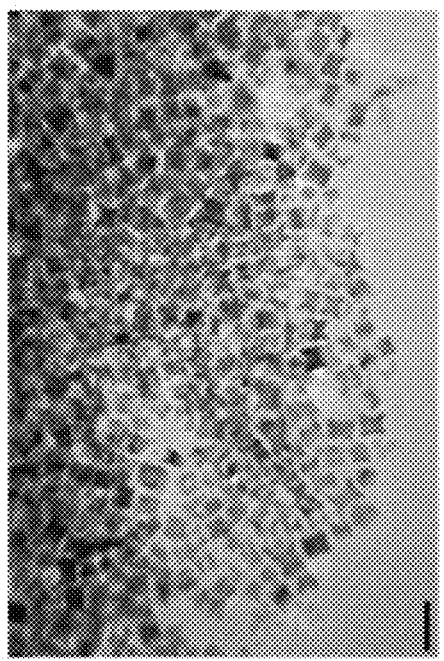
FIG. 3A is a TEM image showing Pd nanocubes.
Figure 3D:
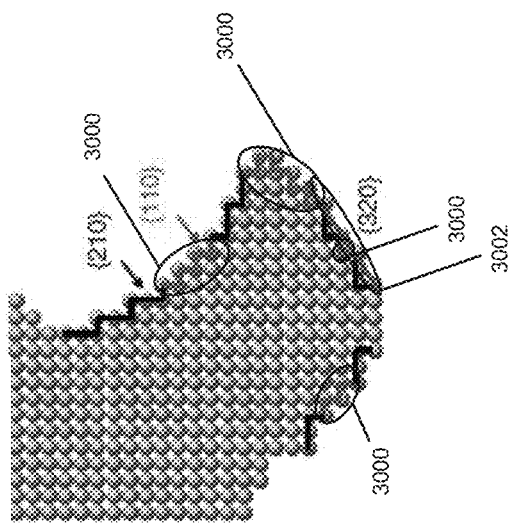
FIG. 3D shows the two-dimensional (2D) lattice modelling corresponding to FIG. 3C.
Figure 3C:
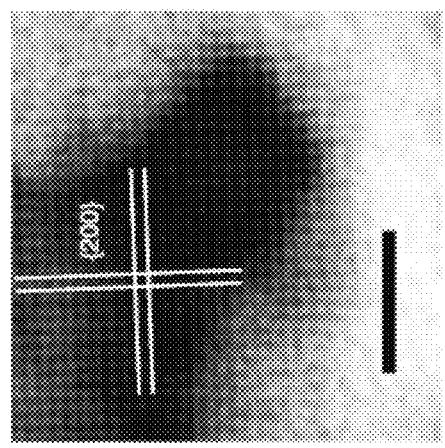
FIG. 3C is a higher magnification of the corner region highlighted of a squared area in FIG. 3B.

The etching treatment was conducted in a reverse micelle system made of CTAB/octanol/$H_2O$. After 20 min residual octanol and excess surfactants were removed by washing with ethanol and water. The edges of Pd NPs were excavated on six faces, while the overall size remained the same as Pd seeds (FIG. 3A, TEM image). A HRTEM image of the Pd concave nanocube in FIG. 3B reveals darker contrasts at the corners, indicating that the sample is thicker at the corners and is thinner in between after the etching treatment. The single crystal characteristics observed along the [100] axis is demonstrated by the corresponding FFT pattern in the inset of FIG. 3B. FIG. 3C shows higher magnification of the corner region highlighted of a squared area in FIG. 3B. A large number of surface atoms are situated at ledge, ledge-kink and kink sites after etching, and it generates complex lattice fringe patterns on the surface. FIG. 3D shows the two-dimensional (2D) lattice modelling corresponding to FIG. 3C, where a high-index {320} plane (line 3002) composed of alternating subfacets of {110} (lines 3000) and {210} (un-circled lines) is tentatively labelled. This result indicates that CTAB did not completely protect these nanocrystals, and desorption of Pd atoms from the seed is predominant while the rate of re-adsorption on lower-energy surfaces is negligible at this early stage of shape evolution. This sparse growth may be attributed to the low concentration of and the low reactivity of Pd species in the hydrophobic solution. After 1 h of further etching treatment, the concaved nanocubes were transformed into hollow nanocages (FIG. 4A). FIG. 4B shows TEM images of individual nanocages at different angles. The average edge length of nanocage is 10 nm, 2 nm shorter than the one for the seed. This suggests that atoms on the corners of seeds started to dissolve into the solution at this aging time. The hollow structure of Pd nanocage was also confirmed from a series of TEM images obtained through tilting the sample stage at a variety of angles. The nearly pure composition of Pd of the nanocage was confirmed using the energy-dispersive X-ray spectrum. While the nanocages are single crystalline in general, some NPs show polycrystalline characteristics. As shown in the HRTEM image of FIG. 4C and its corresponding inverse FFT images (not shown), the edges of the nanocages are imaged along [100], where the (020) and (002) planes of fcc Pd are indexed. Meanwhile, the left upper corner area of the nanocages is imaged along [1-10], and lattice fringes corresponding to (020) and (111) planes of fcc Pd are resolved. A vacancy separating these two crystalline zones is marked with an arrow in FIG. 4D. FIG. 4E shows that lattice fringes corresponding to (020) and (111) planes of fcc Pd at the edge region highlighted with a red square in FIG. 4C. The polycrystalline characteristics are also confirmed by the FFT pattern in the inset of FIG. 4C, where a superposition of [100] and zones are indexed. The observation of shape transformation from nanocubes to concave nanocubes and finally hollow nanocages indicates that the shape evolution occurs thermodynamically so that the etching patterns are consistent with surface energy landscape created by the reorganization in the diminishing reverse micelle compartment. The observation of atomic re-adsorption on the lowest-energy {111} facets with complicated lattice fringes with atoms on ledge, ledge-kink and kink sites (FIG. 4C) becomes more noticeable after 1 h of the shape evolution, probably because of the increased concentration of Pd in solution inducing their re-adsorption on these sites.

As illustrated in FIG. 2A, the shape evolution of seed nanocubes is driven by the structure change of capping layers on seed nanocrystals after water compartment is evaporated in the reverse micelle system. To probe the packing condition of CTAB capped on shaped NPs, Fourier transform infrared spectroscopy is applied to Pd nanocubes before and after etching, where peak positions and widths of C—$CH_2$ asymmetric and symmetric stretching vibrations of the methylene chain of CTAB can be used to assess the nature of surfactant packing on solid surfaces. Compared with the crystalline CTAB both stretching vibrations shift to the higher frequency for CTAB-capped Pd nanocubes (from 2,917 to 2,920 $cm^{-1}$ for the asymmetric band and from 2,849 to 2,851 $cm^{-1}$ for the symmetric band). The lower vibrational frequency and the narrower bandwidth for the crystalline surfactant correspond to more ordered structures of the methylene chains of CTAB. Since the stretching bands for CTAB on Pd nanocubes are blue-shifted relative to crystalline CTAB and their frequencies are comparable to the ones on gold nanorods (2,921 and 2,851 $cm^{-1}$, respectively), CTAB forms a well-defined bilayer capped on Pd nanocubes with less degree of packing order than the crystalline state. Both symmetric and asymmetric bands for CTAB on Pd nanocages are further shifted to 2,922 $cm^{-1}$ and 2,853 $cm^{-1}$, respectively, which indicates that CTAB covers the surface of Pd nanocages with less packing order and surface coverage as compared with Pd nanocubes, yielding a large number of less-protected surface atoms exposed at ledge, ledge-kink and kink sites, consistent with nanoscopic structures in FIG. 4C.

In addition to the effect of the surface energy distribution, desorption of Pd atoms from the seed nanocrystals can be promoted by the formation of stable Pd complexes between desorbed Pd atoms and solute molecules. For confirmation, UV-vis absorption measurements of solution were performed during the shape evolution process. Under the experimental condition, Pd atoms dissolved from {200} facets in octanol can readily oxidized into $CTA^+$ $[PdX_4]^{2-}$ complex species (X=Cl or Br), and a minute amount of the oxidized forms of ascorbic acid residue (for example, semi-dehydroascorbic acid and dehydroascorbic acid) in the Pd seed solution may serve as oxidants. After 1 h of etching and separation of Pd NPs with centrifugation, the remaining supernatant was analysed. While octanol solution containing only CTAB (20 mg $ml^{-1}$) shows no absorption peaks, the spectrum of supernatant shows two peaks at 250 and 340 nm, respectively. Both peaks are corresponded to the ones for $CTA^+$ $[PdX_4^{2-}]$ complex ions. A series of UV-vis spectra of $CTA^+$ $[PdX_4^{2-}]$ with the concentration ranging from 0 to 180 μM in octanol also showed the similar absorption profile, and they follow the Beer-Lambert law. This result suggests that the desorbed individual Pd atoms are highly reactive in solution and they can readily be oxidized and can form the stable complex during the etching treatment. Since the relatively high stability of complexes between Pd atoms and solute molecules promotes the desorption of Pd atoms from Pd nanocubes, types of solvents should also influence the etching process. When the seeds were aged in ethylene glycol, a polar solvent, instead of octanol, NPs were grown in larger sizes while maintaining their cubic shape, indicating that the bilayer capping of CTAB on {200} facets was intact. As no obvious etching was observed on the seed nanocrystals, the reaction rates of dissolving of small NPs and the growth of large NPs are equally high and large NPs grow at the expense of smaller seeds as seen in Ostwald ripening. The faster crystal growth in EG is attributed to the higher reactivity of $CTA^+$ $[PdX_4]^{2-}$ in the polar solvent. When the reaction was conducted in a 1:1 EG/octanol solution, normal Ostwald ripening was still observed; however, NPs no longer maintained their cubic shape. Adding octanol to EG solution increased the hydrophobicity of the solution, and it seems to destabilize the bilayer structure of CTAB on {200} facets of Pd nanocubes so that the shape of NPs became irregular after aging at elevated temperature.

Catalytic Performance and Mechanism

Figure 5A:
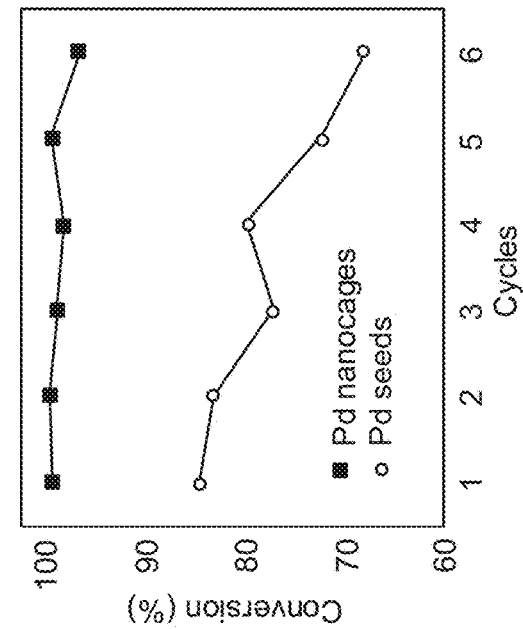
FIG. 5A shows catalytic conversion of iodobenzene using Pd nanocages compared to Pd nanocubes as a function of time.
Figure 5B:
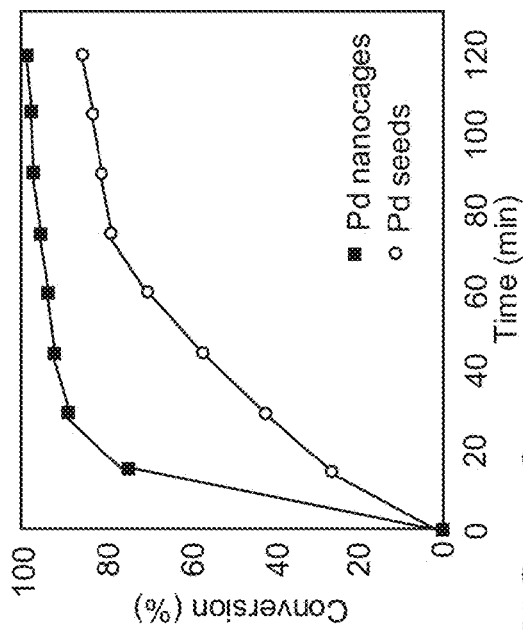
FIG. 5B shows catalytic conversion of iodobenzene using Pd nanocages compared to Pd nanocubes as a function of number of cycles of re-use.
Figure 5C:
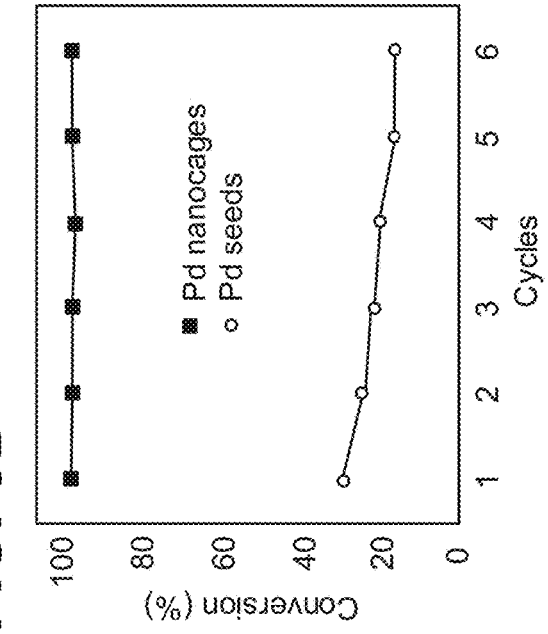
FIG. 5C shows catalytic conversion of iodotoluene using Pd nanocages compared to Pd nanocubes as a function of time.
Figure 5D:
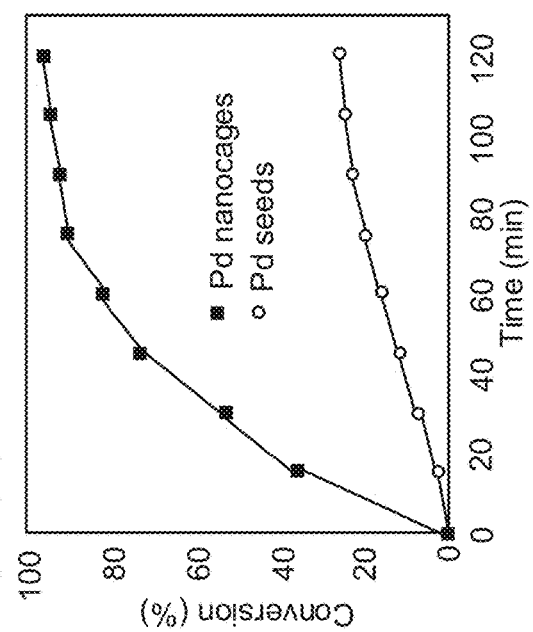
FIG. 5D shows catalytic conversion of iodotoluene using Pd nanocages compared to Pd nanocubes as a function of number of cycles of re-use.

As the hollow Pd nanocages have the large surface area-to-volume ratio and they also exhibit the high density of catalytically active atoms on the ledge, ledge-kink and kink sites, these characteristics prompted us to investigate their potential catalytic performance. To this end, the catalytic activities of 10 nm Pd nanocages and 12 nm Pd nanocubes were compared in Suzuki coupling reactions. First, the coupling between phenylboronic acid ($PhB(OH)_2$) and iodobenzene was investigated in 80% ethanol aqueous solution at room temperature. As shown in FIG. 5A, Pd nanocages show superior catalytic property that a nearly complete formation (greater than 90%) of C—C bond is achieved within 30 min, whereas 12 nm Pd nanocubes can only promote a conversion of about 40% under the same condition and it required 75 min to reach a steady conversion of about 80%. In FIG. 5B, Pd nanocages also demonstrate excellent recycling performance while small loss of catalytic property is observed for Pd nanocubes after several cycles of the reuse. The cumulative turnover number (mol of product per mol Pd) over six runs for Pd nanocages (10 µg, 0.03 mol %) is $1.9 \times 10^4$, which is 1.3 times higher than the one for the Pd nanocubes. To compare them in more difficult catalytic environment, iodobenzene is replaced by iodotoluene, an electron-neutral aryl iodide, which is less reactive in the coupling reaction. As shown in FIG. 5C, the reaction catalysed by Pd nanocages was nearly completed (greater than 90%) after 90 min, while Pd nanocubes could convert only less than 30% of reactants at 50° C. In this harder coupling reaction between $PhB(OH)_2$ and iodotoluene, the turnover number for Pd nanocages (10 µg, 0.03 mol %) remains $1.9 \times 10^4$ over six runs; however, it is 4.5 times higher than the one for Pd nanocubes, and the superior recyclability for Pd nanocages over Pd nanocubes is also demonstrated (FIG. 5D). No homocoupled product was observed during the coupling between $PhB(OH)_2$ and iodotoluene, as supported by nuclear magnetic resonance (NMR) spectra.

It is unlikely that leaching Pd atoms from Pd nanocages catalyse the Suzuki coupling reaction between aryl iodide and $PhB(OH)_2$ because, if Pd atoms are released from Pd nanocages as homogeneous catalysts, deformation of the shape of nanocages along with declined catalytic turnovers should be observed in the recycling process even though some of these Pd atoms are readsorbed on the nanocage. To firmly confirm that no leaching Pd species are involved in the Suzuki coupling reaction, the three-phase test was examined under the standard condition (0.6 mmol $PhB(OH)_2$, 0.3 mmol iodobenzene or iodotoluene, 1 mmol $K_2CO_3$, 10 µg Pd nanocages (0.03 mol %) and 5 ml 80% ethanol aqueous solution) in the presence of NovaSyn TGR resin-supported aryl iodide. While the quantitative recovery of biphenyl products was still achieved in the solution phase, no biphenylamide was detected after cleavage of the resin with trifluoro-acetic acid (TFA) by gas chromatography-mass spectrometry (GC-MS) and NMR. Thus, these results indicate that no free Pd atoms or Pd-organic complexes are involved in the Suzuki coupling reactions in the aqueous solution at relatively low reaction temperature, and the catalytic reactions only take place on the surface of Pd nanocages. The heterogeneous catalytic nature of Pd nanocages indirectly supports the hypothesis above that the superior catalysis is related to the large number of active Pd atoms exposed on the surface.

The dominant desorption of Pd atoms from the center of {200} facets leads to fabrication of hollow NPs with concaved framework, in the size of about 10 nm, less than the size of the seeds. While the overall sizes of individual NPs were decreased relative to seeds in this anisotropic etching treatment, the size distribution was not notably changed because of the survival of low-energy facets on seeds. To turn on the atomic desorption mode for etching, the well-defined packing structures were disordered and their coverage on NPs was reduced via interference with organic solvent after the aqueous compartment of reverse micelle was evaporated (FIG. 2A). Consequently, the surface energy gradient was generated, which could trigger the etching on specific locations on the seed surfaces (FIG. 2A).

To examine whether this approach can be applicable to generate other shaped metal NPs, Au nanocages were synthesized by etching Au nanocube seeds with the same method used for the synthesis of Pd nanocages. The three-dimensional (3D) characteristics of hollowness of Au nanocages were verified with their TEM images at different tilt angles. Thus, this experiment suggests that the atomic desorption-based etching approach can be widely applicable to fabricate a variety of shaped NPs with the simple etching mechanism.

Figure 5E:
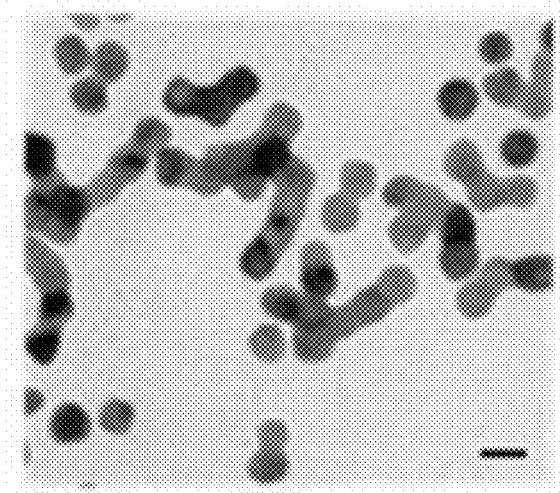
FIG. 5E is a TEM image of Au nanocube seeds before etching in a micelle system. Scale bar=15 nm.
Figure 5F:
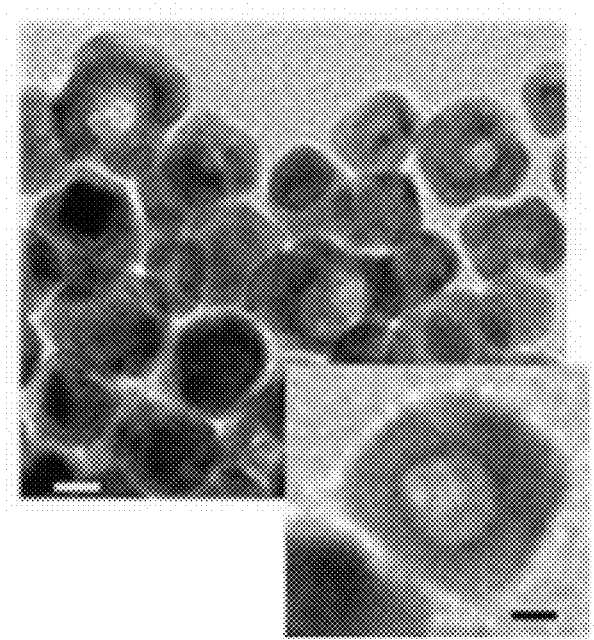
FIG. 5F depicts TEM images of Au nanocages after etching in a micelle system. Scale bar=10 nm. Inset shows high resolution TEM image of nanocages. Scale bar=4 nm. As discussed for Pd nanocage engineering, the growth of hollow structure indicates that tuning surface energy by either ligand exchange or destabilizing the structure at high temperature can give rise to anisotropic growth/etching of nanocube seeds.

The same synthetic approach to engineer Au nanocages may also be conducted in a micelle system. The etching treatment for Au nanocubes follows the similar procedure as for Pd. This process may successfully etch Au nanocube seeds (FIG. 5E) and transformed to Au nanocages (FIG. 5F). Specifically, an aqueous Au nanocube solution (0.2 mg $mL^{-1}$, 200 µL) was added into octanol containing CTAB (20 mg $mL^{-1}$, 5 mL). The solution was heated to 105° C. to evaporate water in the reverse micelles with bubbling of Ar. After 1 h, the products were collected by centrifugation, and washed with ethanol twice and then water three times to remove residue oil and excess surfactants. The products were stored in water at 4° C.

The seed-etching nanofabrication approach for the shape-controlled NPs was designed and demonstrated. The shape evolution from the seed nanocubes to concave nanocubes and finally hollow nanocages were observed by controlling atomic desorption from specific areas of the seed surfaces. The shape evolution occurred thermodynamically, and the etching patterns were consistent with surface energy landscape created by the structure change in reverse micelle reactors. The stability of ion complexes between desorbed Pd ions and solute molecules was also important to promote the atomic desorption mode on the seed nanocubes. The seed-etching process sheds light on the rational design of shape-controlled synthesis of NPs. In addition to the demonstration of Pd and Au nanocage fabrications in reverse micelle reactors in this work, very recently the shape evolution was applied for fabricating platinum-nickel (Pt—Ni)

bimetallic nanoframes by preferentially eroding Ni atoms distributed towards the interior of polyhedral faces of seed nanocrystals via oxidation. Therefore, the shaped NP fabrication via the atomic etching strategy on selected positions of seeds is versatile and it is expected to have broad impacts on a variety of nanotechnological applications. This fabrication strategy is beneficial for a variety of areas such as catalysis, plasmonics, electronics and biomedicine where rational shape-controlled synthesis of NPs in size less than 20 nm has significant impact on their performances. For catalysis, such small complex-shaped NPs are expected to have high catalytic activity because the complex hollow structures of Pd nanocages exhibit a large number of atoms on ledge, ledge-kink and kink sites with high surface areas.

Figure 5G:
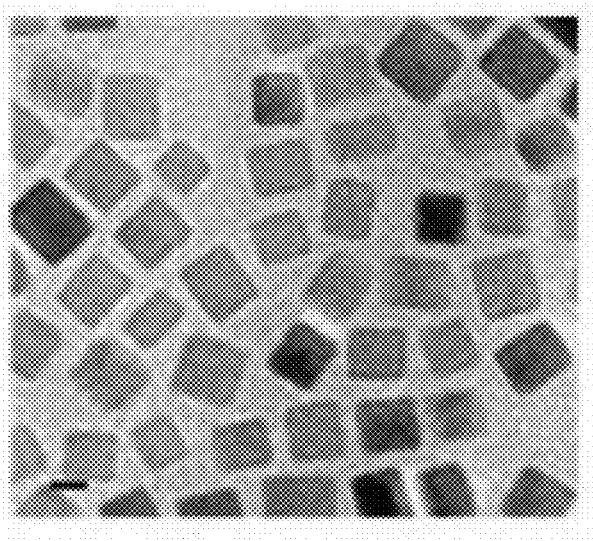
FIG. 5G is a TEM images of iron oxide nanocube seeds before etching in a micelle system. Scale bar=10 nm. Inset shows high resolution TEM image of nanocube seed. Scale bar=4 nm.
Figure 5H:
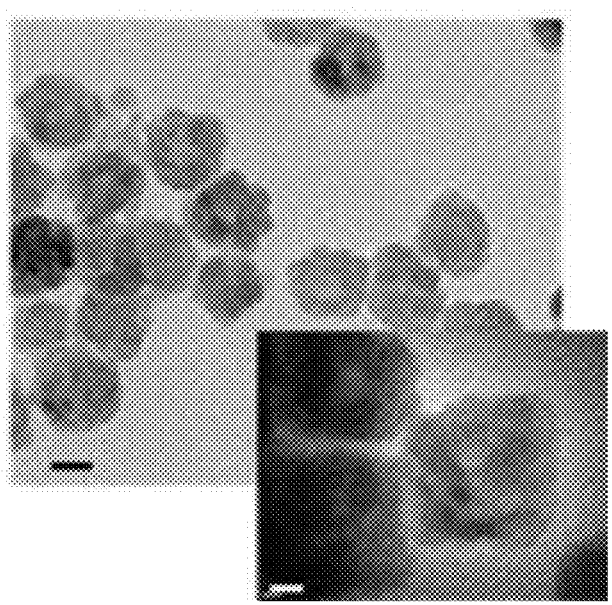
FIG. 5H depicts TEM images of iron oxide nanocages after etching in a micelle system. Scale bar=10 nm. Inset shows high resolution TEM image of nanocages. Scale bar=4 nm. It should be noted that the shape evolution from nanocube to nanocage was not observed without adding aqueous solution (1 mL) containing iron(III) chloride and sodium oleate. The growth of hollow structure indicates that tuning surface energy by either ligand exchange or destabilizing the capping structure at high temperature can give rise to anisotropic growth/etching of nanocube seeds.

The same synthetic approach to engineer iron oxide nanocages may also be conducted in a micelle system made of DTAB/toluene/$H_2O$. This process may successfully etch iron oxide nanocube seeds (FIG. 5G) and transformed to iron oxide nanocages (FIG. 5H. The etching treatment was conducted in a reverse micelle system made of CTAB/octanol/$H_2O$. For the iron oxide nanocage synthesis, a diethylene glycol (DEG) solution (8.0 mL) containing dodecyltrimethylammonium bromide (DTAB), 0.5 g, was heated to 240° C. with vigorous stirring. A toluene solution of $Fe_3O_4$ nanocrystals (1.0 mL) was injected to the hot solution and the system was kept at this temperature for 5 min until the solution became clear. DTAB capped NCs were prepared without further treatment. To promote the shape evolution, aqueous solution (1 mL) containing iron (III) chloride (0.1 M) and sodium oleate (0.3 M) was added to the DEG solution containing DTAB capped NCs. The result solution was aged at 240° C. in air for 1 h. The product was collected by centrifugation and washed with water three times.

The nanoparticle, whose framework can be functionalized by a newly developed porous polymer capping agent, may be used to package a drug inside of the cage and is cable of targeting various tumors and diseases. The nanoparticle can also be used to circulate in bodies for long periods of time and penetrate a blood-brain barrier. In those embodiments where the nanoparticles are iron oxide or other magnetic material, their location can be tracked by magnetic resonance imaging (MM). This iron oxide nanocage can also be used as a drug, as in an alternated magnetic field it can produce heat to kill targeted cells. The resulting nanoparticle may have a new polymer capping that allows various molecules to be conjugated to the nanoparticles by simple chemical reaction(s). This nanoparticle may also have an extremely high stability in a human body due to the strong interaction between that polymer and iron oxide and the porosity of polymer enables drug release from inside the nanocage.

In another exemplary embodiment, to produce the micelles containing the seed nanocrystals inside, an aqueous inorganic/metal nanocube seed solution (1 mg mL$^{-1}$, 200 µL) is stirred and sonicated with octanol containing CTAB (20 mg mL$^{-1}$, 5 mL) for 1 min until the clear solution is obtained. Any organic solvents or aqueous solvents are acceptable for this process, dependent on the structure of micelle microreactor (e.g., the reactor can be oil-in-water droplet or water-in-oil droplet). The solvent in the micelle reactor should have a lower boiling point than the outer solvent. The starting nanocubes can be synthesized using published methods. The starting size of nanocube seed depends on the final-targeted size of nanocage. For example, to produce 8 nm nanocage, the starting nanocube could be 12 nm (i.e., the micelle reactor etches 4 nm while the shape is evolved from cube to cage). After the ultrasonic treatment, the clear micelle system was heated to 105° C. for the evaporation of aqueous phase with bubbling Ar for the etching process (FIG. 2A). After 1 hr of this etching treatment, the concaved nanocubes were transformed into hollow nanocages.

Figure 6:
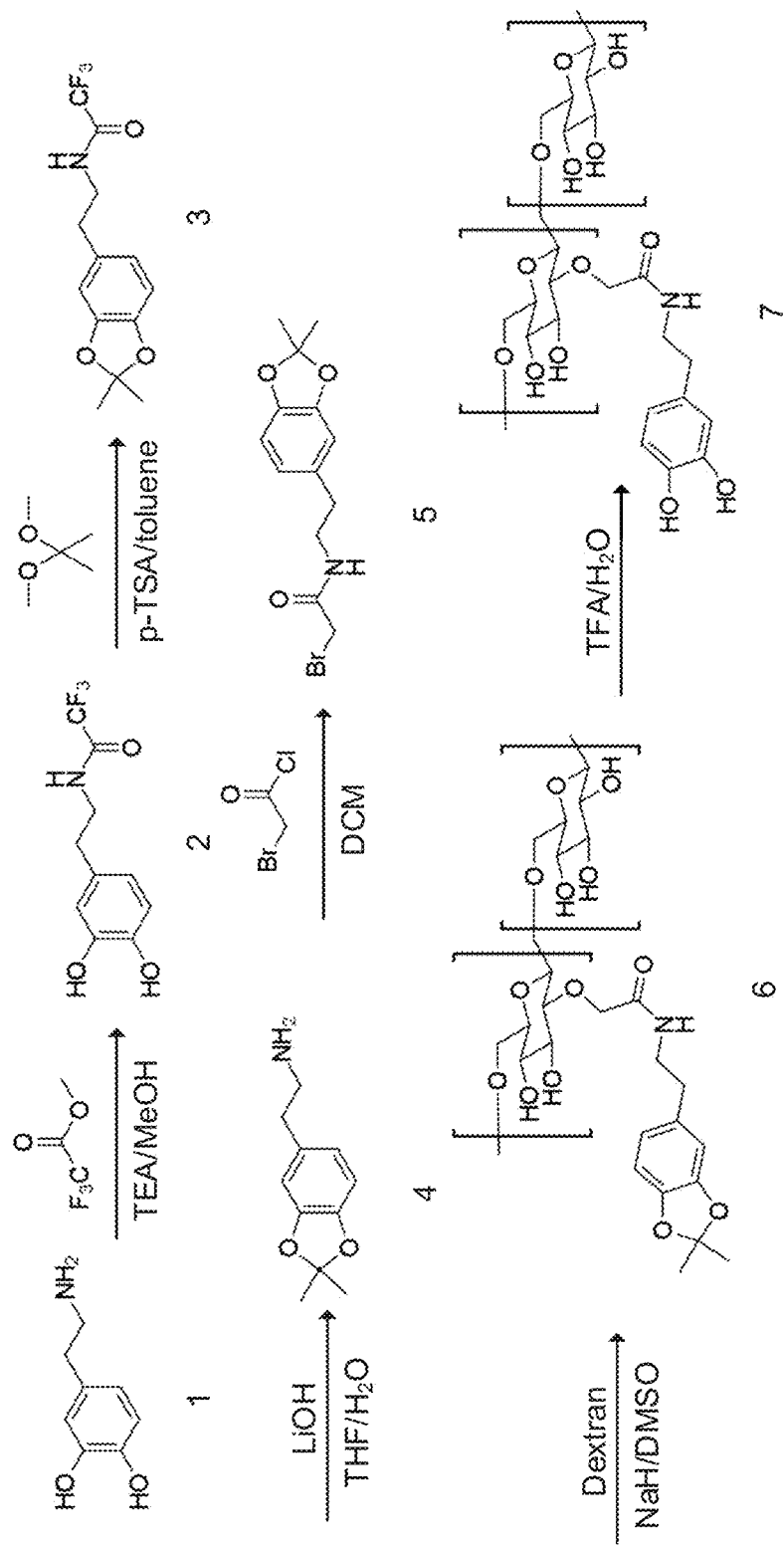
FIG. 6 depicts a synthetic scheme for forming a capping agent of catechol-functionalized dextran.

In some embodiments, the resulting nanocages are coated by biocompatible polymers that not only disperse nanocages without aggregation but also conjugate important molecules for targeted drug delivery such as drugs, antibodies, peptides and proteins. In one exemplary embodiment, dextran is chosen because dextran is porous and this capping does not sacrifice the porous nature of nanocages as drug molecules can still to leak out from the core. Dextran is also proven to be biocompatible, and carboxylic acid groups can conjugate any molecules with the standard amine-carboxylate conjugation reaction. A capping agent of catechol-functionalized dextran was developed for this purpose (FIG. 6). Catechols such as L-dopa and dopamine, discovered in mussel tissues, strongly adhere to metal oxide surfaces, and dextran was synthetically modified with a catechol so that this capping agent is extremely stable on the metal oxide nanocages even in blood flow.

FIG. 6 depicts a product (7) wherein a polymer part (a series of brackets in upper side) is dextran and bottom part is catechol. Previously, dextran was only used to embed many iron oxide nanoparticles in the polymer domain (e.g., FIG. 7A), however dextran has never been capped on single iron oxide nanoparticles. The product (7) enables capping on single iron oxide nanoparticles with strong adhesion of catechol group.

Figure 7A:
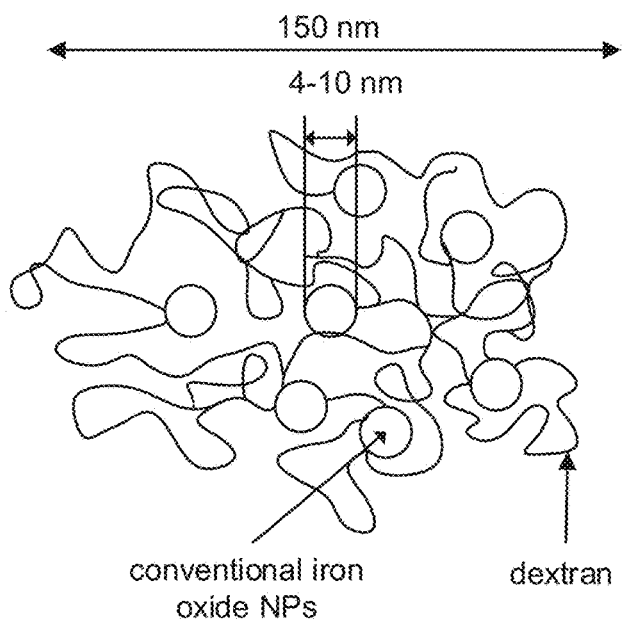
FIG. 7A illustrates iron oxide nanoparticles in the polymer domain of a dextran.
Figure 7B:
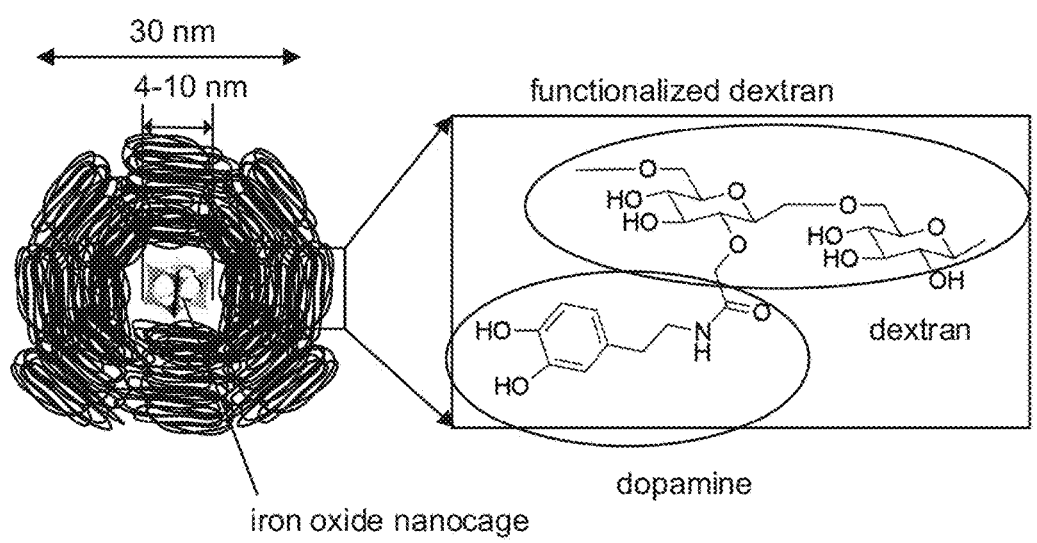
FIG. 7B depicts a structure of dextran-capped iron oxide nanocages.

FIG. 7A depicts commercially available iron oxide nanoparticle-dextran MRI contrast agents such as FERIDEX™. Grown nanoparticles are immobilized on dextran with weak electrostatic interactions. Multiple nanoparticles are attached on the polymer matrix, and sizes of nanoparticles and polymer domain and the number of nanoparticles per dextran domain are difficult to control. FIG. 7B depicts a structure of dextran-capped iron oxide nanocages. The functionalized dextran (in a square in right) with dopamine has a stronger metal binder of catechol group (double OH groups) enabling the capping of individual nanocage as shown in the left. Catechols bind iron oxide nanoparticles with the strong complexation between two OH groups and Fe ions. Dextran has porous networks allowing flows of water molecules and drug molecules in and out. High surface areas and the cavity structure will enhance $T_1$ MRI contrast due to the strong interaction between spins of surface paramagnetic Fe' and protons of water molecules. In contrast with conventional dextran-based agents (e.g. FERIDEX™) the disclosed particles are exceptionally small (e.g. under 50 nm) and remain in the bloodstream longer. In the example of FIG. 7B, the particles are about 30 nm in diameter. Additionally, the dextran provides a polymeric shell around each nanocage which enhances the stability of the nanocage and protects any therapeutic agents (e.g. drugs, genes, etc.) that are disposed within the nanocage.

The following procedure was utilized to develop the catechol-functionalized dextran. First, TFA-dopamine(acetonide) is synthesized as an intermediate from combined published methods. Briefly, dopamine•HCl (1, 4.26 g, 22.5 mmol) was dissolved in 50 mL methanol and the solution was purged for 30 min with $N_2$ gas. Methyl trifluoroacetate (4.6 mL, 46 mmol) and trimethylamine (TEA, 13 mL) was added to the reaction mixture. The mixture was stirred at room temperature overnight. The volatile solvents were removed by rotary evaporation and the residue was treated with HCl to a pH of about 1 and extracted by ethyl acetate. The organic layer was washed with water, dried over $MgSO_4$, and evaporated to give TFA-dopamine (2) in 91% yield. Then, TFA-dopamine (5.0 g, 20 mmol) and 2,2-dimethoxypropane (10 mL, 80 mmol) were dissolved in toluene (200 mL) and stirred under reflux for 10 min. To the reaction mixture p-toluenesulfonic acid monohydrate (104 mg) was added and stirred for 24 h under reflux. After cooling, the volatile solvent was removed by rotary evaporation. The crude product obtained was purified by flash chromatography to give TFA-dopamine(acetonide) (3) in 88% yield. TFA-dopamine(acetonide) (3.0 g, 5.2 mmol) was dissolved in tetrahydrofuran (THF) (20 mL). Lithium hydroxide (LiOH, 2.2 g, 52 mmol) in 10 mL water was added to the reaction mixture. The mixture was stirred at room temperature for 48 h. The THF was subsequently evaporated under reduced pressure, with the residue being re-dissolved in dichloromethane (DCM) and washed with brine, dried over $MgSO_4$, and evaporated to give dopamine (acetonide) (4) in 91% yield.

Bromoacetyl chloride (416 μL, 5 mmol) was added dropwise to a solution of dopamine(acetonide) (0.91 g, 4.7 mmol) and triethylamine (767 μL, 5.5 mmol) dissolved in DCM (20 mL) at 0° C. in an ice-bath. The cooling bath was then removed and the reaction mixture was stirred at room temperature overnight. The reaction mixture was washed sequentially with 1 N HCl, saturated aqueous $NaHCO_3$ solution, and water and then dried over anhydrous $MgSO_4$. After the solvent was removed by rotary evaporation, the crude product obtained was further purified by flash chromatography to give α-bromoacetamide (5) in 64% yield. Dextran (200 mg) was dissolved in 25 mL DMSO, and the solution was added in a flame-dried 100 mL round-bottom flask under argon. To this solution, sodium hydride (NaH, 60% in oil, 0.06 g, 1.6 mmol) was added portion wise slowly under magnetic stirring. The mixture continued to be stirred for 20 min. Tetrabutylammonium iodide, (TBAI, 2.6 mg, 0.007 mmol) and α-bromoacetamide (0.324 g, 1.03 mmol) were added and the mixture was heated at 60° C. overnight. The product was precipitated in cold ethanol, washed with ethanol, and dried in vacuo to give dextran-dopamine(acetonide) (6) in 78% yield. To deprotect hydroxyl groups dextran-dopamine(acetonide) (0.15 g) was dissolved in 5 mL 90% v/v trifluoroacetic acid (TFA) in $H_2O$. The solution was stirred at room temperature overnight. The volatile solvents were removed under vacuum, and the raw product was dialyzed against $H_2O$ for 48 h. Then, the solution was lyophilized to give the product (7) in 100% yield.

Figure 8:
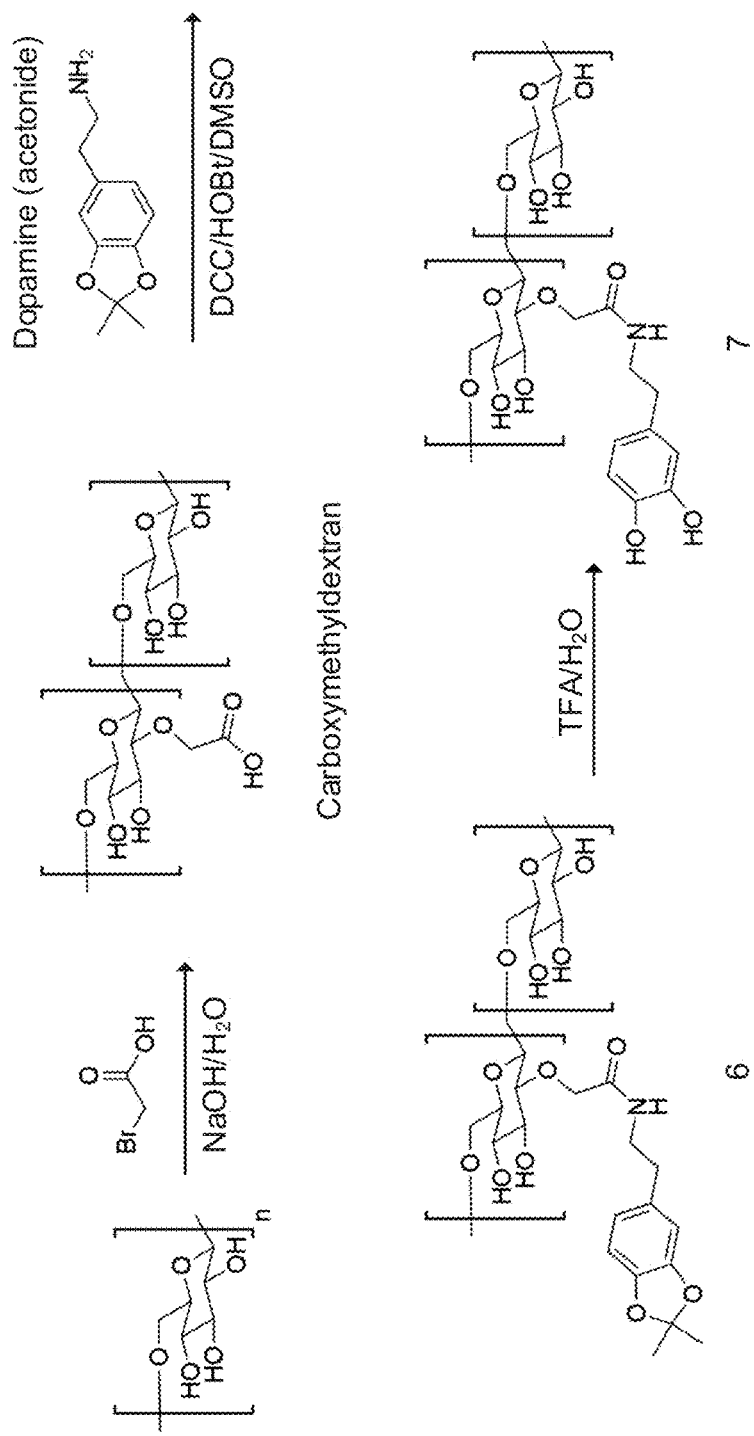
FIG. 8 depicts an alternative method for conjugating dopamine(acetonide) to dextran.

An alternative method for conjugating dopamine(acetonide) to dextran is as follows (FIG. 8). In this approach, dextran (2 g) was dissolved in 10 mL NaOH (1 N) aqueous solution containing bromoacetic acid (1.39 g, 10 mmol). The solution was stirred at room temperature overnight, and dialyzed against 0.1 N HCl for 24 h followed with $H_2O$ for 48 h. Then, the solution was lyophilized to produce carboxymethyldextran (CMD). CMD (0.8 g) and 1-hydroxybenzotriazole (HOBt, 0.383 g, 2.5 mmol) were dissolved in 20 mL DMSO at 0° C. on ice. Then, dicyclohexylcarbodiimide (DCC, 0.516 g, 2.5 mmol) was added under magnetic stirring, and the cooling bath was removed to allow the reaction to proceed at room temperature for 10 min. Next, dopamine(acetonide) (0.48 g, 2.5 mmol) was added, and the reaction was carried out at room temperature overnight. The precipitated byproduct, dicyclohexylurea, was removed by filtration, and the product was precipitated in cold ethanol, collected by centrifugation, washed with ethanol three times, and dried in vacuo to yield dextran-dopamine(acetonide) (6) in 76% yield. Dextran-dopamine(acetonide) (6) (0.15 g) was dissolved in 5 mL 90% v/v trifluoroacetic acid (TFA) in $H_2O$. The solution was stirred at room temperature overnight. The volatile solvents were removed under vacuum, and the raw product was dialyzed against $H_2O$ for 48 h. Then, the solution was lyophilized to produce the product (7) in 100% yield.

The product catechol-functionalized dextran can be dissolved in water, DMSO, or other appropriate solvents, and it can be combined with inorganic nanocages dispersed in hexane or other organic solvents to undergo ligand exchange and make inorganic nanocages water-soluble. After this treatment, inorganic nanocages are capped by the catechol-functionalized dextran. The physical and chemical properties of the catechol-functionalized dextran-capped nanocages can be controlled by modifications to the dextran such as the degree of catechol-functionalization. The number of catechols per dextran can be controlled by adjusting the molar ratio of catechol and dextran precursors in FIG. 6 and FIG. 8. In FIG. 8, amine groups of catechol are conjugated with carboxylic acid groups of dextran; when the number of catechols is saturated by binding all available carboxylic acid groups of dextran, the dextran monomer-catechol ratio is 2:1. When these carboxylic acid groups of dextran are not saturated, unused carboxylic acid groups can be applied to conjugate other molecules, drugs, and peptides that display amine groups at the end. This functionalization strategy allows one to produce multifunctionalized dextrans, for instance, including dyes and radioactive molecules for contrast agents in medical imaging or antibodies for targeting specific cells.

Figure 9:
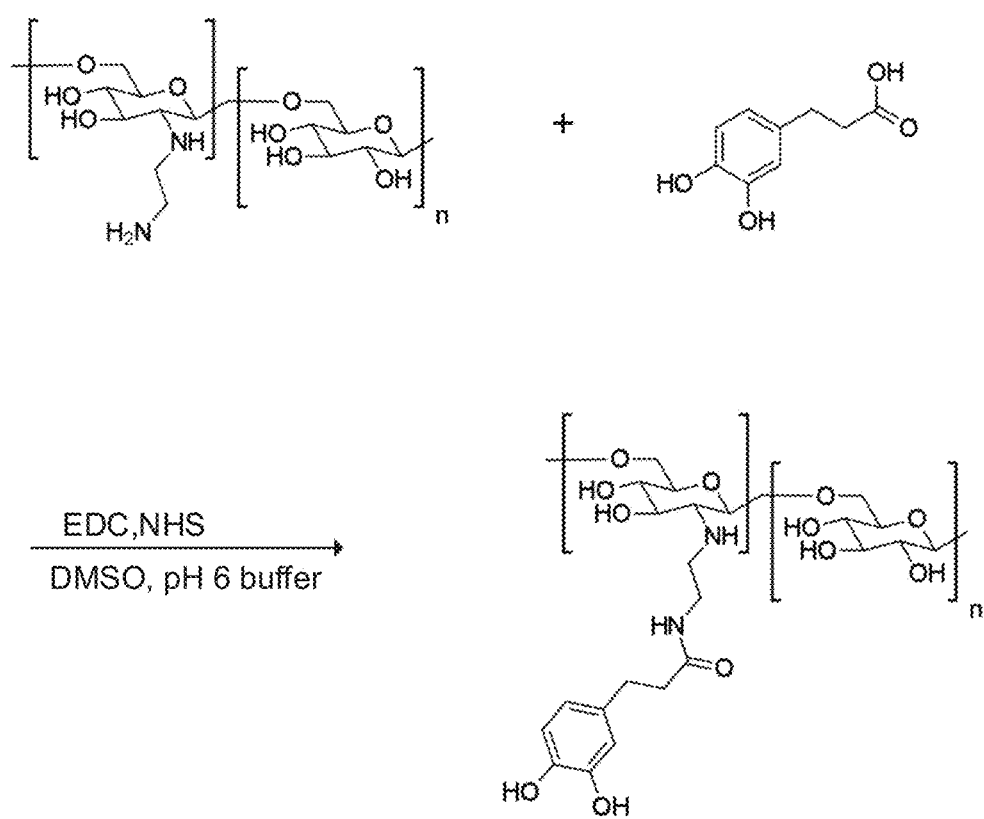
FIG. 9 depicts another protocol to synthesize the catechol-conjugated dextran by conjugating aminodextran and carboxylate catechol.

Another protocol was developed to synthesize the catechol-conjugated dextran like FIG. 7B by conjugating aminodextran and carboxylate catechol (FIG. 9). Aminodextran can be obtained through reductive amination or by other methods, is commercially available, and can contain a variable number of amino groups per monomer. 3,4-dihydroxyhydrocinnamic acid (DHCA), 3,4-dihydroxyphenylacetic acid (DOPAC), or other similar compounds can be used for the carboxylate catechol in FIG. 8. In a typical preparation, 100 mg (2.5 μmol) aminodextran (molecular weight 40 KDa, 10 amines per molecule), 4.6 mg (25 μmol) DHCA, 4.8 mg (25 μmol) 1-ethyl-3-[3-dimethylaminopropyl]carbodiimide (EDC), and 2.9 mg (25 μmol) N-hydroxysuccinimide (NHS) were dissolved in 1 mL dimethyl sulfoxide and 1 mL pH 6 buffer containing 0.1M 2-(N-morpholino)ethanesulfonic acid (MES) and 0.5M NaCl and reacted overnight. The catechol-dextran was condensed with ethanol and collected by centrifugation. The pellet was dissolved in 1 mL $H_2O$ with sonication, then frozen and lyophilized. This product can be dissolved in a solvent such as DMSO or water and added to a suspension of inorganic nanocages or any other nanoparticles to cap them for chemical functionalization, drug internalization, and/or prevention of aggregation. The amount of catechol capping can be controlled, dependent on the desired protection of internalized molecules. For example, if the internalized molecules need to be released fast, the amount of capping can be reduced, while the increased capping slows the release rate.

The catechol-dextran in FIG. 8 has one catechol group per two dextran groups. For the catechol-dextran in FIG. 9, there is one amine group of catechol per twenty dextran monomers. Thus, if amine groups of dextran are fully substituted by catechols, one catechol possesses 20 dextran monomers (i.e., less catechol per dextran for the compound in FIG. 9 as compared to the one in FIG. 8). By adjusting the molar ratio of catechol and dextran precursors, amine groups left unsubstituted can be used for conjugation with other molecules that display carboxylic acid groups. Catechol groups are specifically bound to iron oxide nanoparticles with high affinity. While more catechol groups on dextran are expected to stabilize the capping on iron oxide nanocages more, dynamic light scattering shows that the catechol-dextran in FIG. 9 is more disperse in aqueous solutions.

For use in certain medical applications, capping agents on nanoparticles should be firmly fixed on the nanoparticles to avoid their degradation and aggregation during the circulation in a human body. However capping agents should also not block water molecule flow in and out the cavity of nanocages for brightening MRI contrasts. Dextran is a hydrophilic polymer that has porous polymeric networks for fine water circulation, however the commercialized contrast agents such as FERIDEX™ are made by growing iron oxide nanoparticles on dextran aggregates (e.g., iron oxide nanoparticles are embedded in the polymer matrix in random distribution with weak electrostatic interactions, FIG. 7A) because the binding force of commercial dextran with iron oxide nanoparticles is not strong enough to cap individual nanoparticles. As explained elsewhere in this disclosure, the monodispersity of nanoparticle size in the controlled domain size is desirable for their application as super-high resolution MIII contrast agents. Therefore, a better approach is to grow nanoparticles first in the uniform size and then cap them with well-defined porous frameworks. Protein cages were applied as monodisperse frameworks for capping iron oxide nanoparticles, but in this disclosure we use the dextran polymer as a capping agent because of the porous character for higher water molecule flow. To overcome the issue of weak binding of dextran with iron oxide, we modify dextran to have a binding group of catechol (FIG. 7B). Catechol on dopamine binds iron oxide nanoparticles with higher affinity than other well-used capping agents such as polyethylene glycol (PEG) due to the strong complexation between two OH groups and Fe ions. The bidentate OH ligands and Fe ions bond covalently with both σ- and π-bonding. Thus, the strong binding affinity of catechol group will anchor the modified dextran on such small curvature of nanoparticles whose size is less than 10 nm as shown in FIG. 7B if dextran is conjugated with dopamine. Using this capping approach, iron oxide nanocages can amplify MRI contrast by the porous hydrophilic polymer coating via further improved water molecule flows and the stable immobilization, in comparison to iron oxide particles. It should be noted that carboxylic groups on dextran allows one to conjugate many molecules such as drugs, antibodies, and biomarkers via standard amine-carboxyl conjugation reaction, which distinguishes this capping from other polymer coatings. Dextran is conjugated with dopamine (see FIG. 7B) based on a method described above.

Methods

Chemicals. Sodium tetrachloropalladate(II) ($Na_2PdCl_4$, 99.995%), gold(III) chloride hydrate ($HAuCl_4$, ≥9% Au basis), sodium hydroxide (NaOH, ≥8%), sodium borohydride ($NaBH_4$, ≥99%), CTAB (≥99%), ascorbic acid (≥99.0%), 1-hydroxybenzotriazole hydrate (HOBt, 99%), N,N'-diisopropylcarbodiimide (DIC, 99%), acetic anhydride ($Ac_2O$, 99.5%), ethanol (≥99.5%), methanol (MeOH, ≥99.5%), 1-octanol (≥99%), dichloromethane ($CH_2Cl_2$, ≥99.9%), ethyl acetate (EtOAc, ≥99.8%), tetrahydrofuran (THF, ≥99.9%), EG (≥99%), N,N-dimethyl-formamide (DMF, ≥99%), pyridine (≥99.9%), iodobenzene (98%), 4-iodotoluene (≥99%), 4-iodobenzoic acid (98%), biphenyl-4-carboxamide (96%), phenylboronic acid ($PhB(OH)_2$, 498%), deuterated chloroform ($CDCl_3$, 99.8%), deuterated dimethyl sulfoxide (DMSO-$d_6$, 99.9%), TFA (≤99.0%), potassium carbonate ($K_2CO_3$, ≥99.0%) and magnesium sulphate ($MgSO_4$, ≥99.5%) were all purchased from Sigma-Aldrich, and were used as received without further purification except THF, which was distilled to remove butylated hydroxytoluene (BHT). NovaSyn TGR resin (0.25 mmol g$^{-1}$ loading) was purchased from EMD Millipore. Sartorius ultrapure water (18.2 MΩ cm) was used in all preparations.

Synthesis of Pd nanocubes. The 12 nm Pd nanocube seeds were synthesized in the modified method on the basis of report by Niu et al. (ACS Nano 4, 1987-1996 (2010) and Cryst. Growth Des. 8, 4440-4444 (2008)) Typically, 600 μl of 30 mM $Na_2PdCl_4$ solution and 200 μl of 500 mM NaOH were added to 10 ml of 12.5 mM CTAB solution under stirring. After the solution was heated at 95° C. for 10 min, 200 μl of freshly prepared 500 mM ascorbic acid solution was added. The reaction was allowed to proceed for 30 min. Then, the product was separated using centrifugation and washed with water. The as-prepared Pd seeds were stored in water at 4° C.

Synthesis of Au nanocubes. Au nanocubes were synthesized using the seed-mediated method according to Chen et al. (Langmuir 24, 5233-5237, (2008)) In a typical seed synthesis, a freshly prepared, ice-cold aqueous $NaBH_4$ solution (0.01 M, 0.3 ml) was added into an aqueous mixture solution composed of $HAuCl_4$ (0.01 M, 0.125 ml) and CTAB (0.1 M, 3.75 ml). The solution was mixed by rapid inversion for 2 min, and then kept at room temperature for 1 h before use. In a typical growth reaction, CTAB (0.1 M, 6.4 ml), $HAuCl_4$ (0.01 M, 0.8 ml) and ascorbic acid (0.1 M, 3.8 ml) were sequentially added into $H_2O$ (32 ml). Twenty microliters of the CTAB-stabilized seed solution were diluted 10 times with water and then added into the growth solution. The resulting solution was mixed by gentle inversion for 10 s and then left undisturbed overnight. The product was separated using centrifugation and washed with water. The as-prepared Au nanocubes were stored in water at 4° C. and used as seeds for the etching experiment.

NP etching. The seed-etching treatment was conducted under argon (Ar) to avoid oxidation of Pd into PdO. In the typical experiment, an aqueous Pd seed solution (1 mg ml$^{-1}$, 200 μl) was added into octanol containing CTAB (20 mg ml$^{-1}$, 5 ml). A clear reverse micelle system made of CTAB/octanol/$H_2O$ was formed with stirring and ultrasonic treatment, where Pd seed NPs were dispersed in the water phase. Subsequently, the solution was heated to 105° C. to evaporate water in the reverse micelles with bubbling of Ar. It should be noted that no additional etchant was added into the reaction system. A set of products in a variety of shapes with different etching time was collected using centrifugation and washed with ethanol twice, and then water was added three times to remove residue oil and excess surfactants. The products were stored in water at 4° C.

The etching treatment for Au nanocubes follows the similar procedure as for Pd. Specifically, an aqueous Au nanocube solution (0.2 mg ml$^{-1}$, 200 μl) was added into octanol containing CTAB (20 mg ml$^{-1}$, 5 ml). The solution was heated to 105° C. to evaporate water in the reverse micelles with bubbling of Ar. After 1 h, the products were collected using centrifugation and washed with ethanol twice and then water three times to remove residue oil and excess surfactants. The products were stored in water at 4° C.

Catalytic evaluation in Suzuki coupling reactions. Suzuki coupling reaction was performed according to procedures in previous reports (Angew. Chem. Int. Ed. 50, 7850-7854 (2011) and J. Am. Chem. Soc. 133, 1106-1111, (2010)). For the catalytic synthesis of biphenyl compounds, $PhB(OH)_2$ (73 mg, 0.6 mmol) was added to ethanol (4 ml) with iodobenzene (34 µl, 0.3 mmol) or iodotoluene (65 mg, 0.3 mmol) in the presence of $K_2CO_3$ (138 mg, 1 mmol) and aqueous solutions containing Pd NPs (1 ml, 10 µg ml$^{-1}$, 0.03 mol %). Reactions were carried out under vigorous stirring at room temperature for iodobenzene and 50° C. for iodotoluene, respectively. The biphenyl product and unreacted aryl iodides (if any) were extracted with $CH_2Cl_2$ (3×5 ml), while the excess $PhB(OH)_2$ and Pd NPs remained in the aqueous layer. The organic layer was then washed with saturated $K_2CO_3$ solution three times, and it was dried over $MgSO_4$ powders. After filtration, $CH_2Cl_2$ was removed through rotary evaporation. The products were dissolved in $CDCl_3$ and analysed with 1HNMR. For the reaction between iodobenzene and $PhB(OH)_2$, the percentage yield was calculated by comparing the integration of the peak at δ 7.4 p.p.m. (biphenyl) with that at δ 7.1 p.p.m. (unreacted iodobenzene). For coupling of iodotoluene with $PhB(OH)_2$, the integration of the peaks at δ 7.5 p.p.m. (4-methylbiphenyl) and δ 6.9 p.p.m. (unreacted iodotoluene) was used to calculate the percent yield. Pd NPs from the aqueous layers were recycled using centrifugation and then dispersed in 1 ml $H_2O$. To evaluate the recyclability of catalysts, the reactions were examined by mixing fresh reagents with the recycled Pd NP solutions.

Preparation of NovaSyn TGR resin-supported aryl iodide. 4-iodobenzoic acid (0.149 g, 0.6 mmol), HOBt $H_2O$ (0.092 g, 0.6 mmol) and DIC (94 µl, 0.6 mmol) were pre-mixed in DMF (5 ml) on ice for 1 h. Then, NovaSyn TGR resin 1 (0.48 g, 0.25 mmol g$^{-1}$ loading) was added. The reaction was conducted by stirring overnight at room temperature. A capping solution consisting of $Ac_2O$ (45 µl, 0.48 mmol) and pyridine (42 µl, 0.52 mmol) was added, and the reaction was allowed for an additional 30 min. The product, resin 2, was separated by filtration and washed with DMF (3×5 ml), MeOH (3×5 ml) and $CH_2Cl_2$ (3×5 ml) and dried under vacuum. The resin was stored at −20° C. before use.

Three-phase test. Suzuki coupling reactions were performed under standard condition (0.6 mmol $PhB(OH)_2$, 0.3 mmol iodobenzene or iodotoluene, 1 mmol $K_2CO_3$, 10 µg Pd nanocages (0.03 mol %) and 5 ml 80% ethanol aqueous solution) in the presence of resin 2 (42 mg, 0.01 mmol). Reactions were carried out under vigorous stirring at room temperature for iodobenzene and 50° C. for iodotoluene, respectively. After 2 h, the resin was separated by filtration. While the conversion of iodobenzene or iodotoluene in the filtrate was analyzed as described in 'Catalytic Evaluation in Suzuki Coupling Reactions', the insoluble resins were purified by washing with $H_2O$ (3×2 ml), MeOH (3×2 ml), EtOAc (3×2 ml), THF (3×2 ml) and $CH_2Cl_2$ (3×5 ml). Here resin 2 would convert to resin 3 if any active homogeneous catalyst appears in the solution during the coupling reaction. This conversion can be verified by analyzing the compounds after cleavage with TFA, where 5 and 6 were cleavage products of 2 and 3, respectively. To this end, the resin was treated with 2 ml 95% v/v TFA in $CH_2Cl_2$ for 30 min at room temperature. The cleavage solution was filtrated and the resin was washed with $CH_2Cl_2$ (3×2 ml), EtOAc (3×2 ml) and THF (3×2 ml). The combined filtrates were evaporated. The product was dissolved in THF and analyzed with GC-MS. In this sample, dodecane was added as an internal standard. The product was also confirmed with 1HNMR after dissolving in DMSO-$d_6$.

Characterization. TEM images were captured on a JEM 2100 microscope (JEOL Inc) with an acceleration voltage of 200 kV. Samples were prepared by drying 2 µl of the NP solution on carbon-coated copper grids under ambient condition. UV-vis absorption spectra were recorded on Beckman Coulter DU 800 UV/Vis Spectrophotometer. $^1$HNMR spectra were recorded on Bruke 500 MHz spectrometers. Chemical shifts (δ values) were reported in p.p.m. downfield from internal tetramethylsilane.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A composition of matter comprising:
    an inorganic nanocage with a diameter less than 15 nm, wherein the inorganic nanocage comprises palladium, iron oxide or gold;
    a polymer shell comprising dextran surrounding the inorganic nanocage, wherein the polymer shell has a diameter of less than 50 nm and the inorganic nanocage is covalently attached to the polymer shell by a dopamine.

2. The composition of matter as recited in claim 1, wherein the inorganic nanocage is a gold nanocage.

3. The composition of matter as recited in claim 1, wherein the inorganic nanocage is a palladium nanocage.

4. A composition of matter comprising:
    an iron oxide nanocage with a diameter less than 15 nm;
    a polymer shell comprising dextran surrounding the inorganic nanocage, wherein the polymer shell has a diameter of less than 50 nm and the iron oxide nanocage is covalently attached to the polymer shell by a dopamine.

* * * * *